(12) United States Patent
Wiesener

(10) Patent No.: US 11,291,855 B2
(45) Date of Patent: Apr. 5, 2022

(54) DEVICE FOR FEEDING A LINE THROUGH THE SKIN OF A PATIENT

(71) Applicant: Berlin Heart GmbH, Berlin (DE)

(72) Inventor: Constantin Wiesener, Potsdam (DE)

(73) Assignee: BERLIN HEART GMBH, Berlin (DE)

( * ) Notice: Subject to any disclaimer, the term of this patent is extended or adjusted under 35 U.S.C. 154(b) by 498 days.

(21) Appl. No.: 16/315,481

(22) PCT Filed: Jul. 5, 2017

(86) PCT No.: PCT/EP2017/066842
§ 371 (c)(1),
(2) Date: Jan. 4, 2019

(87) PCT Pub. No.: WO2018/007473
PCT Pub. Date: Jan. 11, 2018

(65) Prior Publication Data
US 2019/0232084 A1 Aug. 1, 2019

(30) Foreign Application Priority Data
Jul. 7, 2016 (EP) .................................... 16178481

(51) Int. Cl.
*A61N 5/06* (2006.01)
*A61M 39/02* (2006.01)
(Continued)

(52) U.S. Cl.
CPC .......... *A61N 5/0624* (2013.01); *A61L 2/0029* (2013.01); *A61L 2/0076* (2013.01); *A61L 29/14* (2013.01); *A61L 29/16* (2013.01); *A61M 39/02* (2013.01); *A61M 39/0247* (2013.01); *A61M 39/08* (2013.01); *A61M 39/16* (2013.01);
(Continued)

(58) Field of Classification Search
CPC ................ A61N 5/0624; A61N 5/0601; A61N 2005/0662; A61L 2/029; A61L 2/08; A61M 2039/0285; A61M 2039/167; A61M 39/16
See application file for complete search history.

(56) References Cited

U.S. PATENT DOCUMENTS 5,904,646 A 5/1999 Jarvik
6,013,918 A 1/2000 Bushnell et al.
(Continued)

FOREIGN PATENT DOCUMENTS

CN 1448194 A 10/2003
EP 0 082 596 A1 6/1983
WO WO 00/07933 A1 2/2000

OTHER PUBLICATIONS

Brucker et al., English Translation of WO 0007933 (Google Patents). (Year: 2021).*
(Continued)

*Primary Examiner* — Nathan R Price
*Assistant Examiner* — Tasnim Mehjabin Ahmed
(74) *Attorney, Agent, or Firm* — Crowell & Moring LLP

(57) ABSTRACT

A device for feeding a line through the skin of a patient, wherein the line contains a photodynamic substance that releases highly reactive oxygen derivatives when irradiated. Thus, disinfection/sterilization can be achieved in the region of a feed-through both on the outside of the skin and in the feed-through region by irradiating the feed-through.

12 Claims, 3 Drawing Sheets

(51) Int. Cl.
*A61M 39/08* (2006.01)
*A61L 29/14* (2006.01)
*A61L 2/00* (2006.01)
*A61L 29/16* (2006.01)
*A61M 39/16* (2006.01)
*A61N 5/067* (2006.01)

(52) U.S. Cl.
CPC ........... *A61N 5/0601* (2013.01); *A61N 5/062* (2013.01); *A61L 2300/216* (2013.01); *A61L 2300/224* (2013.01); *A61L 2300/404* (2013.01); *A61M 2039/0285* (2013.01); *A61M 2039/167* (2013.01); *A61M 2205/0238* (2013.01); *A61M 2205/051* (2013.01); *A61N 5/067* (2021.08); *A61N 2005/0612* (2013.01); *A61N 2005/0662* (2013.01)

(56) References Cited

U.S. PATENT DOCUMENTS

| 2002/0035386 | A1  | 3/2002  | Whitehurst |
| 2008/0125838 | A1  | 5/2008  | Francis |
| 2009/0292357 | A1* | 11/2009 | McCoy ............... G02B 1/10 623/6.56 |
| 2013/0006194 | A1  | 1/2013  | Anderson et al. |
| 2016/0243334 | A1* | 8/2016  | Da Silva ............... A61M 39/16 |

OTHER PUBLICATIONS

English translation of Chinese Office Action for Application No. CN 201780049056.8, dated Dec. 18, 2020, 16 pgs.

English translation of International Search Report, issued in International Application No. PCT/EP2017/066842, dated Aug. 17, 2017, pp. 1-2, European Patent Office, Rijswijk, Netherlands.

* cited by examiner

DEVICE FOR FEEDING A LINE THROUGH THE SKIN OF A PATIENT

CROSS-REFERENCE TO RELATED APPLICATIONS

This application is a 371 nationalization of international patent application PCT/EP2017/066842 filed Jul. 5, 2017, which claims priority under 35 USC § 119 to EP patent application 16178481.4 filed Jul. 7, 2016. The entire contents of each of the above-identified applications are hereby incorporated by reference.

TECHNICAL FIELD

The invention is in the field of medical technology may be used with particular advantage in implantation medicine. Applications are also possible in other areas of medical technology in which a targeted sterilization and/or disinfection of tissue is desirable.

DETAILED DESCRIPTION

Figure 1:
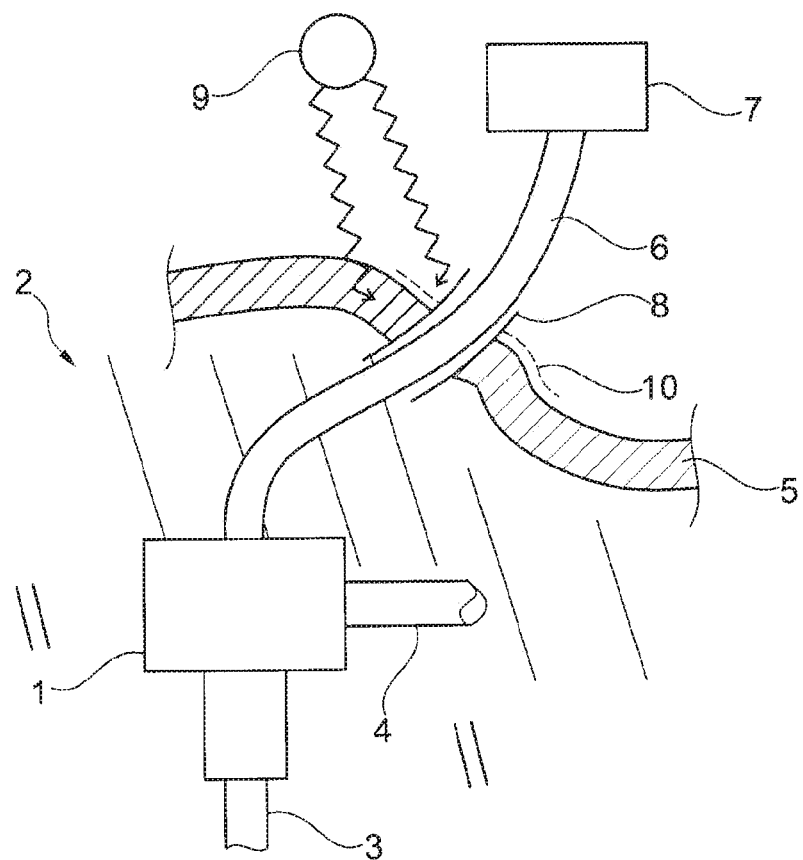
FIG. 1 is a schematic depiction of an implanted heart pump that is connected to a control unit outside the patient's body.

In many areas of medicine in which tissue of a living patient comes into contact with foreign bodies or substances that are not from the body, the targeted sterilization and/or disinfection of such articles or substances is desirable. Many such substances or articles may be thoroughly disinfected/sterilized prior to use. However, it may in particular still be useful even to be able to sterilize/disinfect during or after use on the patient's body. For example, in the case of lines in the form of cannulas or electrical lines that are fed through the skin or tissue of a patient between the exterior region of the body and the interior region of the body, occasionally infections develop in the transition region or in the interior region of the body. These may lead to serious complications in wound healing and/or when operating the corresponding line. Such problems may be treated with externally or internally administered antibiotics; however, over time such treatments lead to the development of resistance or, in the case of multi-resistant microbes, such treatments may already be unpromising.

Given the background of the prior art, the underlying object of the present invention is to provide an effective disinfection option that may be activated both preventively and during the operation of an article or a substance that is brought into contact with the tissue of a patient. The range of microbes that may be treated should be as great as possible, and no new resistances should be developed.

Known from U.S. Pat. No. 5,904,646 A is an implantable actuator for which an infection-resistant cable is used. In this case, in particular a fastening means is provided that connects the cable to a bone of the patient in order to minimize movements of the cable relative to the tissue of the patient.

Consequently, the invention relates to a device for feeding a line through the skin of a patient. The objective is reached in that the line has a photodynamic substance that releases highly reactive oxygen derivatives when irradiated.

A photodynamic substance is a substance that contains a photosensitive substance that is excited by light of a suitable wavelength in the visible spectrum and produces reactive oxygen derivatives in the presence of oxygen. This is possible through two photooxidative processes:

First, using a photooxidative process, radicals may be formed that react with oxygen and form oxidation products. The direction of the electron transfer is determined by the redox potential between the photosensitizer and oxygen.

Secondly, following the light excitation of the photosensitive substance, energy may be transmitted directly onto oxygen atoms/molecules, causing the formation of the highly reactive singlet oxygen that reacts immediately with corresponding target structures that are in close proximity to it.

Substances from the chemical group of phenothiazines, phthalocyanines, and porphyrins may be used for the photosensitizer in order to inactivate both multidrug resistant gram-positive and gram-negative bacteria. The resultant reactive or highly reactive oxygen derivatives have a highly disinfectant/germicidal effect.

One advantage of the invention is that the photosensitive substance (photosensitizer) may be activated in a targeted manner using irradiation in the visible spectrum. In this way active germ treatment is possible even during use in the body of a patient without risking further damage to the organic tissue. Even the location of the action on the photosensitizer may be selectively chosen using appropriate orientation of the radiation. The corresponding highly reactive oxygen may also inactivate multidrug resistant microbes for which antibiotics are no longer effective or have a very poor effect.

The concentration and/or distribution of the photosensitive substance may also be designed such that the substance may be irradiated multiple times at a temporal interval to release highly reactive oxygen. Different photosensitive substances may also be added simultaneously, which substances are sensitive, for example, to different radiation wavelengths, so that the device may be used multiple times.

The line that has the photodynamic substance may, on the one hand, be an electrical line that has one or a plurality of electrical leads and a sheath of the leads, for example in the form of cable sheathing. However, the line may also be one or a plurality of cannulas or tube-like elements, each of which has hollow spaces for conducting liquids or gases.

In both cases the photodynamic substance may be arranged, for example, in the sheath or in the casing of the line so that the sheath/casing of the line comprises, at least in part, a photodynamic substance or is coated with a photodynamic substance. For example, it may be that a photodynamic substance is mixed into the material for the sheath/casing or that macroscopic inlays made of a photodynamic material are added to the material of the sheath/casing. For example, one or a plurality of strands made of a photodynamic substance may be integrated into the casing along the line.

It may likewise be provided that a casing of the line, at least on a sub-segment of its length, consists entirely or partially of a photodynamic substance. In this case, even when a line is disposed in the patient's body, the highly reactive oxygen may be produced/released in the photodynamic substance using simple irradiation with suitable light, for example at a predefined wavelength or a predefined wavelength range, in order to begin the germicidal process.

It may be required, for example, that even in the case of an ingrown line, a portion of the irradiated light irradiates the tissue/skin of the patient and travels to regions of the line that are disposed below the surface of the skin so that the photodynamic substance may even be activated there.

If a covering device in the form of a wound covering is provided at the site of the line entry into the tissue of the patient's body, at least part of this covering device/cuff may be permeable for irradiation activating the photodynamic substance. The irradiation in question may be in the visible spectrum, but the sensitive wavelength range may also be in the infrared or ultraviolet range.

The covering device may be designed to be transparent overall for such irradiation, but it may also have appropriate windows for irradiation with light.

The photosensitive/photodynamic material should be selected such that, with appropriate irradiation, a photooxidative process occurs in the photodynamic substance.

Another selection criterion for a photosensitive/photodynamic substance may be that radicals that react with oxygen occur in the photodynamic substance.

It may also be provided that the photodynamic substance is embodied such that it is photonically excitable, wherein during deexcitation from the excited state energy may be transmitted directly to oxygen and singlet oxygen is produced.

In addition, the invention may consist in the photodynamic substance being a phenothiazine, phthalocyanine, or porphyrin, or a mixture of two of these three components.

Another option for using the invention may provide that a light guide device is provided, at least a segment of which runs at least in some segments inside the line or parallel thereto and from which light may be decoupled for irradiating the line. In this case, using the light guide device, the light for activating the photodynamic substance may be guided in a particularly simple manner to the location where antibacterial treatment appears necessary.

The light guide device may comprise, for example, an optical waveguide that is integrated into the line or guided parallel thereto. Light may be coupled into the optical waveguide at an incoupling site by means of a light source, for example a laser, and the light may either be conducted to the opposing end of the optical waveguide or at least some of the light may be decoupled over the course of the optical waveguide. Inhomogeneities in the edge region of the optical waveguide, for example, such as notches or surface wrinkling, or curves in the waveguide, may be provided for the decoupling. Inhomogeneities in the region of the optical waveguide may usefully be provided along its length, in which optical waveguide activation of a photodynamic substance may presumably be useful. The irradiated light may be reflected at the opposing end of the optical waveguide opposing the light source, for example, in order to minimize losses.

If a line with an optically transparent casing is used, a light guide device may also be placed within the line so that it can irradiate the casing/sheath of the line from the inside.

The invention may also relate to an implantation device having an implant, for instance a heart pump or another unit, a transcutaneous line with a device for feed-through, as described above, and a functional element connected to the line outside of the patient's body, such as for example a power supply or data processing device. Likewise, a blood pump that is coupled to blood vessels and/or parts of a patient's heart by means of fluid lines having one or a plurality of implanted docking elements may be provided outside of the patient's body.

A method for implementing the invention may be provided, for instance, in that a sheath of the line that contains a photodynamic substance is irradiated with light. To this end, a light source that is oriented towards the regions to be disinfected or is connected to the regions to be disinfected by means of an optical waveguide is turned on and operated. The light source is then turned off after the disinfection has been carried out or is oriented towards other regions.

The invention is described in greater detail and explained in the following using figures in the drawings.

Figure 2:
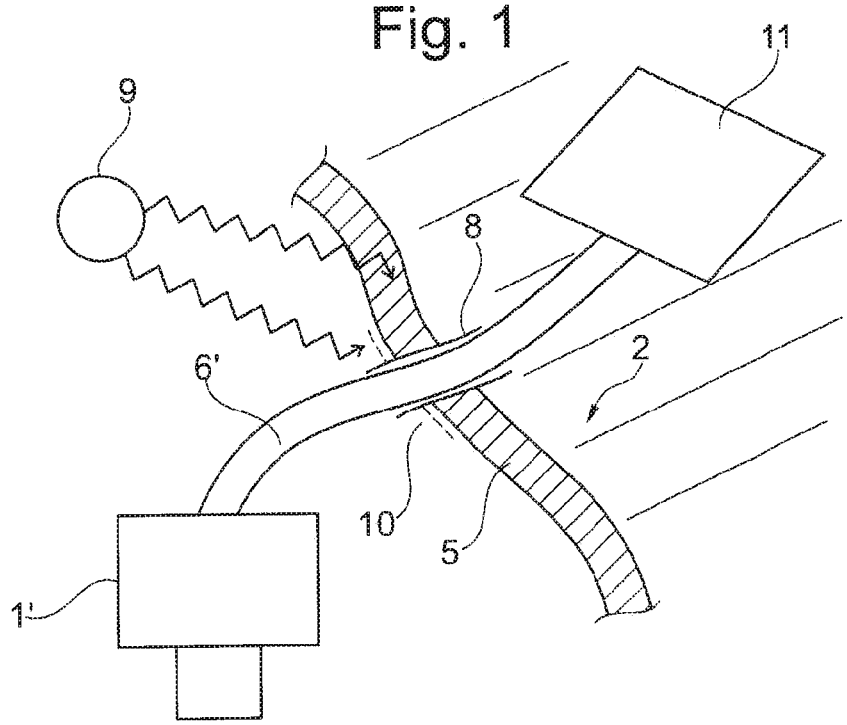
FIG. 2 depicts a pump that is arranged outside the patient's body and that is connected to a patient's heart.
Figure 3:
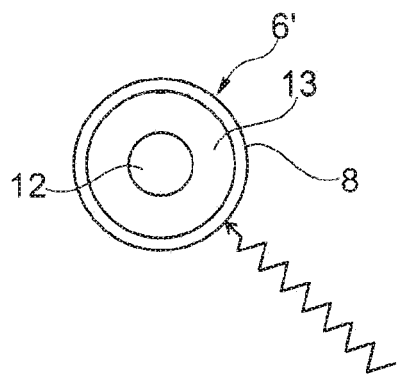
FIG. 3 is a cross-section of a first line.
Figure 4:
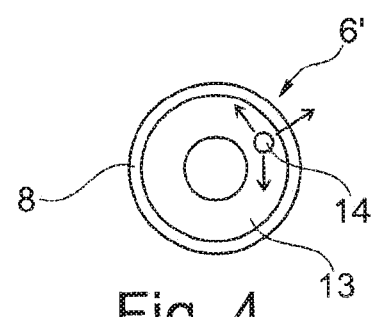
FIG. 4 is a cross-section of a second line.
Figure 5:
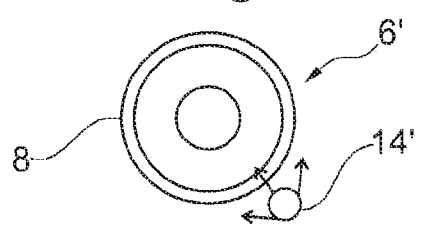
FIG. 5 is a cross-section of a third line having an optical waveguide running parallel thereto.
Figure 6:
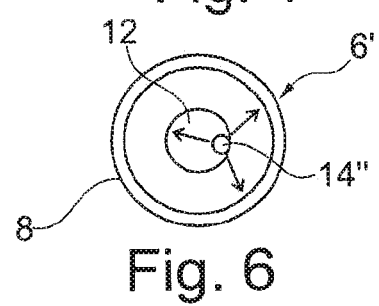
FIG. 6 is a cross-section of a fourth line.
Figure 7:
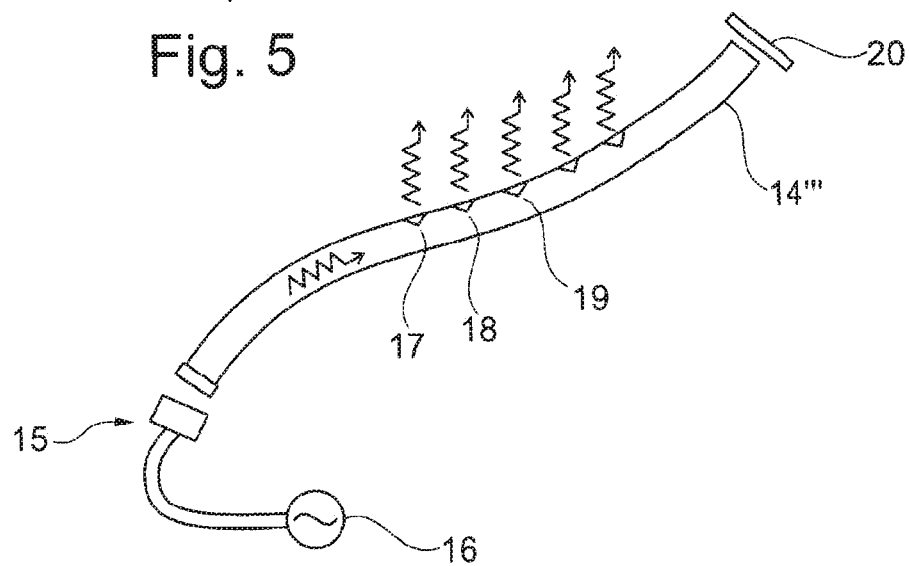
FIG. 7 depicts a view of an optical waveguide having a light source.
Figure 8:
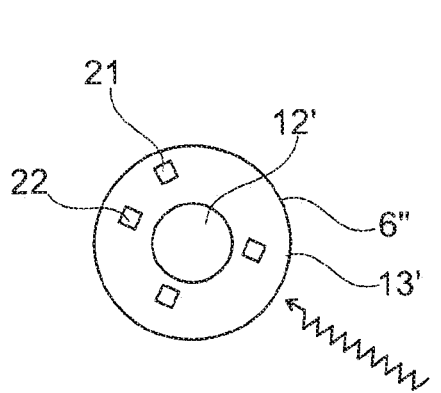
FIG. 8 is a cross-section of a fifth line.
Figure 9:
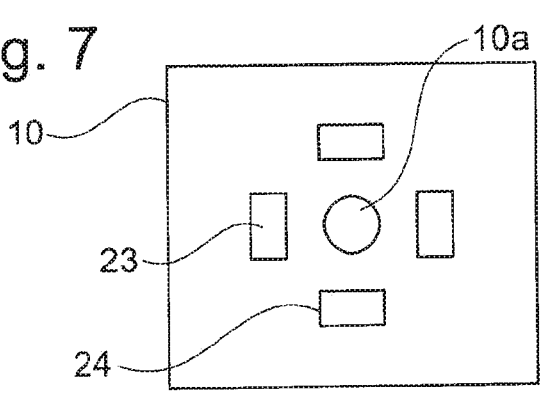
FIG. 9 depicts a wound covering.
Figure 10:
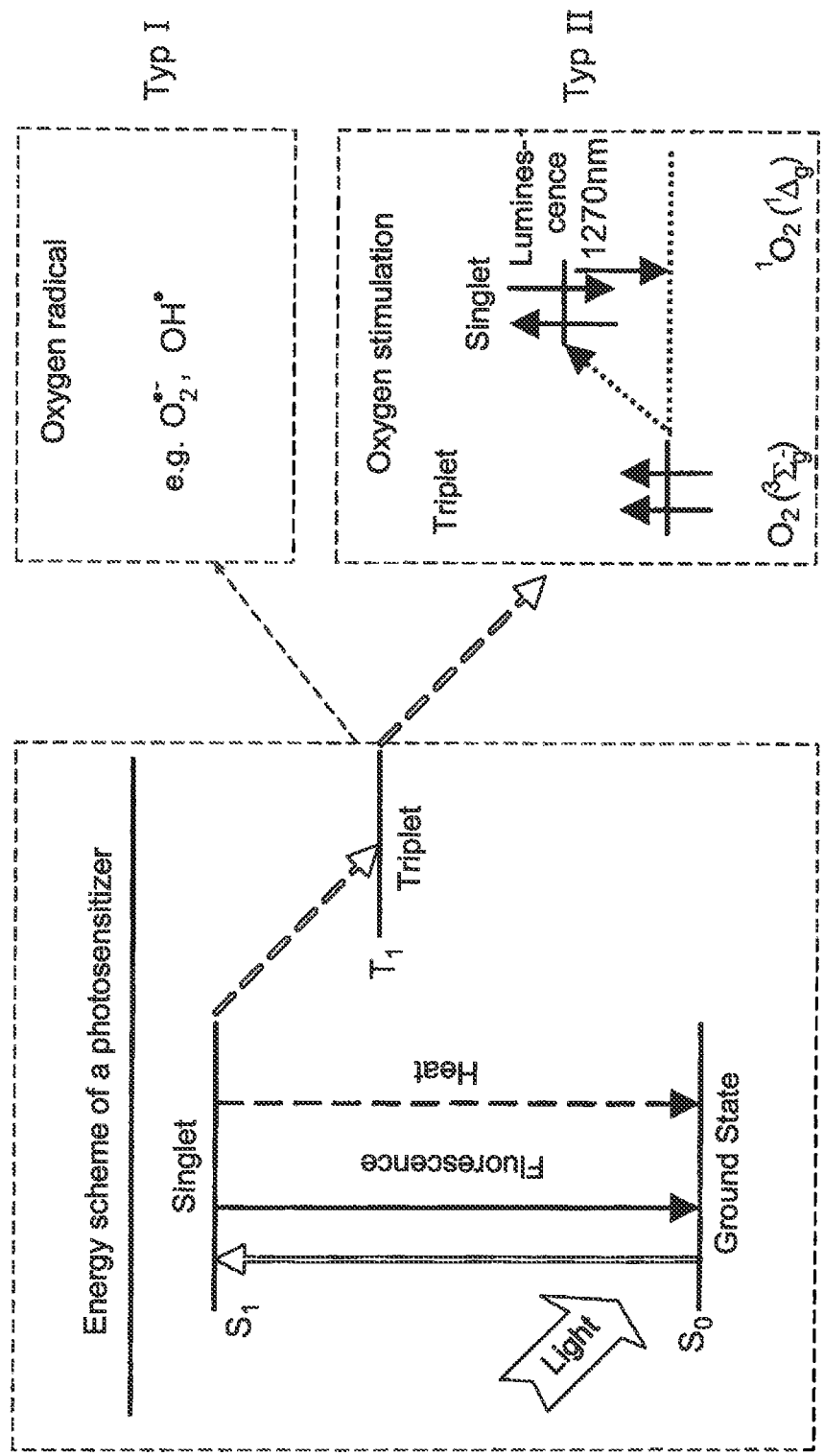
FIG. 10 is a schematic depiction of the photodynamic effect.

FIG. 1 is a schematic depiction of an implanted heart pump that is connected to a control unit outside the patient's body;

FIG. 2 depicts a pump that is arranged outside the patient's body and that is connected to a patient's heart;

FIG. 3 is a cross-section of a first line;

FIG. 4 is a cross-section of a second line;

FIG. 5 is a cross-section of a third line having an optical waveguide running parallel thereto;

FIG. 6 is a cross-section of a fourth line;

FIG. 7 depicts a view of an optical waveguide having a light source;

FIG. 8 is a cross-section of a fifth line;

FIG. 9 depicts a wound covering; and,

FIG. 10 is a schematic depiction of the photodynamic effect.

FIG. 1 depicts a heart pump 1 that is implanted in the body 2 of a patient. The pump inlet 3 and the pump outlet 4 are shown solely for the sake of comprehensiveness; the further course of cannulas is not shown.

The body 2 of the patient is sealed to the outside by the abdominal wall 5. A line 6 feeds through the abdominal wall 5 and contains one or a plurality of electrical leads that are individually or collectively enclosed by one or a plurality of cable sheathings. The pump 1 is connected to a control unit 7 by means of the line 6. In the region of the feed-through through the abdominal wall 5, the line 6 is provided with a coating 8 made of a photodynamic material, which coating covers both a part of the exposed line 6 outside of the patient's body and a region of the line below the abdominal wall 5 inside the patient's body.

Also indicated is a light source 9 that emits light so that when light is absorbed the photodynamic material 8 releases highly reactive oxygen for disinfecting in the coated region of the feed-through of the line 6.

The coating with the photodynamic material may also terminate on the outside of the abdominal wall 5 and be provided solely in the interior of the patient's body.

The entry opening through the abdominal wall 5 is covered by means of a wound covering 10 that is intended to protect the feed-through region from environmental influences and microbes. The covering 10 (depicted with a broken line) may be embodied such that it permits irradiation from the light source 9 to pass through it to the coating 8. For its part, the wound covering 10 may have a coating made of a photodynamic material on its side facing the patient's body so that, when appropriately irradiated with light, disinfection can also take place there in the region of the skin of the patient.

FIG. 2 depicts a pump 1' for cardiac support that is arranged outside of the patient's body 2 and is connected to the heart 11 of the patient by means of a line 6'. The line 6' is essentially formed by a cannula through which blood is pumped between the heart 11 and the pump 1'. The line 6' passes through the abdominal wall 5 or even, for example, another part of the skin of the patient and in the region of the feed-through is provided with the coating 8 made of a photodynamic material. A wound covering 10 is depicted with a broken line above the feed-through opening for the line 6', as in FIG. 1. This wound covering should be permeable for the irradiation from the light source 9, which radiation is required for activating the photodynamic substance. However, it is also possible for the wound covering 10 to be removed for the irradiation.

FIG. 3 depicts one possible cross-section of a line 6' having a central hollow space 12, a cannula wall 13, and an outer coating 8 made of a photodynamic material.

FIG. 4 depicts a cross-section of a cannula similar to that in FIG. 3, wherein integrated into the wall 13 of the cannula is an optical waveguide 14 that is designed to emit light radially. Thus the coating 8 may be irradiated with light from the optical waveguide 14 in order to produce the photodynamic effect.

FIG. 5 depicts a cannula 6' with an optical waveguide 14' that is conducted parallel thereto and that may be glued, for example, to the exterior of the cannula 6'. The optical waveguide 14' radiates light radially and the light may be absorbed by the coating 8 made of a photodynamic substance.

FIG. 6 depicts a cannula 6' in which an optical waveguide 14" is guided in the center hollow space 12 and can radiate radially light that may be absorbed by the photodynamic layer 8.

FIG. 7 depicts an example of an optical waveguide that is designed to radiate light radially. Optical waveguides are usually constructed such that they radiate as little light radially as possible, but instead guide said light only axially and with as little loss as possible. However, if there are regions of major curvature (of a small curvature radius) or notches or surface wrinkling in the outer region on the casing surface of the optical waveguide 14''', at that location light is radially decoupled and may be used for irradiating a cannula running parallel to the optical waveguide. In FIG. 7, a light source, in the form of a laser, for example, is indicated with 15 and is powered by an energy source 16. Light is coupled into the optical waveguide 14''' through the laser and is decoupled radially through the notches 17, 18, 19, depicted schematically. In order to obtain a greatest possible light yield for the radial irradiation, the axially traveling light may be reflected back into the optical waveguide 14''' at a mirror 20.

FIG. 8 depicts a cannula 6" having a center hollow space 12', wherein the wall 13' of the cannula comprises a plastic in which particles 21, 22 made of a photodynamic substance are inlayed. In this case it is possible to do without coating the cannula 6" with a photodynamic material in the casing region. A requirement for this, however, is that the wall 13" of the cannula is permeable for the highly reactive oxygen and/or that the inlayed particles 21, 22 are disposed far enough in the radially outer region of the cannula wall 13' that the highly reactive oxygen released there can travel to the casing surface of the cannula 6".

FIG. 9 depicts a top view of a wound covering 10 that has a center opening 10a for feeding through the line 6, 6', 6" and has optical windows 23, 24 that are for irradiating with light the region of the cannula thereunder if the material for the wound covering 10 is not itself permeable for this radiation. However, the entire covering 10 may comprise material transparent to light so that the photodynamic substance may be activated through the wound covering 10.

FIG. 10 is a schematic depiction of the energy scheme of a photodynamic material (photosensitizer). If the photosensitizer is irradiated with an appropriate light or radiation of a suitable wavelength, the oxygen that is a component of the photodynamic substance or that is arranged in its immediate vicinity is changed from a ground state to a singlet state (singlet oxygen). The singlet oxygen may return to the ground state using fluorescence and releasing heat, but may also return to a triplet state ($T_1$). From this triplet state, in a first reaction form (type I) there may be a charge transfer between an excited PS (photosensitizer) in the $T_1$ state and a substrate molecule, wherein an electron or a hydrogen atom is transmitted. Super oxide anion radicals or hydroxyl radicals are created.

From the triplet state $T_1$ it is also possible for a second reaction (type II) to occur with a direct transfer from the excited PS to oxygen. This leads to the relaxation of the photosensitizer, but also to electronic oxygen excitation from the ground state (triplet state) to the lowest singlet state. This very reactive singlet state is also called singlet oxygen. Both reactions, type I and type II, lead to the release of substances that can be very effective germicides.

The invention may be used advantageously in implantation medicine and not only in the region for feeding through lines, but also for all types of interactions between foreign bodies and a patient's body in which microbes may be introduced. For example, it is possible to coat surgical sutures with a photodynamic material or to produce them in part from such a material. This may represent an independent invention, as does the coating of prostheses in the field of dentistry or even in the field of prostheses for extremities that project at least in part out of the body of a patient.

The invention claimed is:

1. A device for feeding a line through skin of a patient, the device comprising:
    a line, wherein the line comprises a photodynamic substance that releases highly reactive oxygen derivatives when irradiated; and
    a light guide device, wherein the light guide device is configured to decouple light causing irradiation of the line, and the light guide device includes an optical waveguide and inhomogeneities are provided in an edge region of the optical waveguide for decoupling light from the optical waveguide.

2. The device according to claim 1, wherein a sheathing of the line comprises the photodynamic substance.

3. The device according to claim 1, wherein a sheathing of the line, at least on a sub-segment of its length, comprises the photodynamic substance.

4. The device according to claim 1, wherein a covering device comprising a cuff is connected to the line, and wherein the covering device is permeable to irradiation activating the photodynamic substance.

5. The device according to claim 1, further comprising an energy source, wherein the energy source is configured to irradiate the photodynamic substance causing a photooxidative process to occur.

6. The device according to claim 5, wherein the photodynamic substance comprises radicals that react with oxygen.

7. The device according to claim 5, wherein the energy source is configured to photonically excite the photodynamic substance into an excited state, wherein the photodynamic substance is configured to deexcite from the excited state causing energy to be transmitted directly to oxygen and causing singlet oxygen to be produced.

8. The device according to claim 1, wherein the photodynamic substance comprises a phenothiazine, a phthalocyanine, a porphyrin, or a combination thereof.

9. The device according to claim 1, wherein the line comprises a cannula configured to conduct fluids.

10. The device according to claim 1, wherein the line comprises an electrical line with a cable sheathing.

11. The device according to claim 1, wherein the light guide device is configured to run inside at least a segment of the line.

12. The device according to claim 1, wherein the light guide device is configured to run parallel to the line.

* * * * *